(12) United States Patent
Jennings et al.

(10) Patent No.: US 11,602,633 B2
(45) Date of Patent: Mar. 14, 2023

(54) METHOD AND APPARATUS FOR CONTROLLING MULTI-SITE NEUROSTIMULATION

(71) Applicant: PATHMAKER NEUROSYSTEMS INC., Boston, MA (US)

(72) Inventors: Gerald Jennings, Chelsea, MA (US); Andrew Ferencz, Southboro, MA (US)

(73) Assignee: PATHMAKER NEUROSYSTEMS INC., Boston, MA (US)

( * ) Notice: Subject to any disclaimer, the term of this patent is extended or adjusted under 35 U.S.C. 154(b) by 402 days.

(21) Appl. No.: 16/658,495

(22) Filed: Oct. 21, 2019

(65) Prior Publication Data

US 2020/0206504 A1 Jul. 2, 2020

Related U.S. Application Data

(60) Provisional application No. 62/748,684, filed on Oct. 22, 2018.

(51) Int. Cl.
*A61N 1/36* (2006.01)
*A61N 1/20* (2006.01)
*A61N 1/04* (2006.01)

(52) U.S. Cl.
CPC ....... *A61N 1/36034* (2017.08); *A61N 1/0456* (2013.01); *A61N 1/20* (2013.01)

(58) Field of Classification Search
CPC .... A61N 1/36034; A61N 1/0456; A61N 1/20; A61N 1/0551; A61N 1/205; A61N 1/36062
See application file for complete search history.

(56) References Cited

U.S. PATENT DOCUMENTS

| | | | |
|---|---|---|---|
| 9,409,023 B2 | 8/2016 | Burdick et al. | |
| 2009/0132003 A1 | 5/2009 | Borgens et al. | |
| 2013/0053922 A1* | 2/2013 | Ahmed | A61N 1/0551 607/45 |
| 2015/0196767 A1* | 7/2015 | Ahmed | A61N 1/205 607/48 |
| 2018/0071525 A1 | 3/2018 | Ahmed | |
| 2018/0243555 A1* | 8/2018 | Kilgore | A61N 1/0492 |
| 2020/0147389 A1* | 5/2020 | Boor | A61N 1/378 |

OTHER PUBLICATIONS

ISA/US; International Search Report/Written Opinion dated Jan. 22, 2021 in corresponding International Application PCT/US20/56473; 9 pages.

* cited by examiner

*Primary Examiner* — Allen Porter
*Assistant Examiner* — Natasha Patel
(74) *Attorney, Agent, or Firm* — Peter J. Mikesell; Schmeiser, Olsen & Watts, LLP

(57) ABSTRACT

The present invention improves control of currents in a multi-site direct current neurostimulation system. Precise control incorporates three constant current sources in a system consisting of spinal, polarizing and peripheral circuits. Constant current sources (sinks) are placed on the high side of the peripheral circuit and one sink in series on the low side of the spinal circuit in a four electrode configuration, for maintaining both predetermined currents, and current ratios, as the electrode/skin impedance and body impedance vary over the course of a treatment. Resistive steering is also implemented.

20 Claims, 12 Drawing Sheets

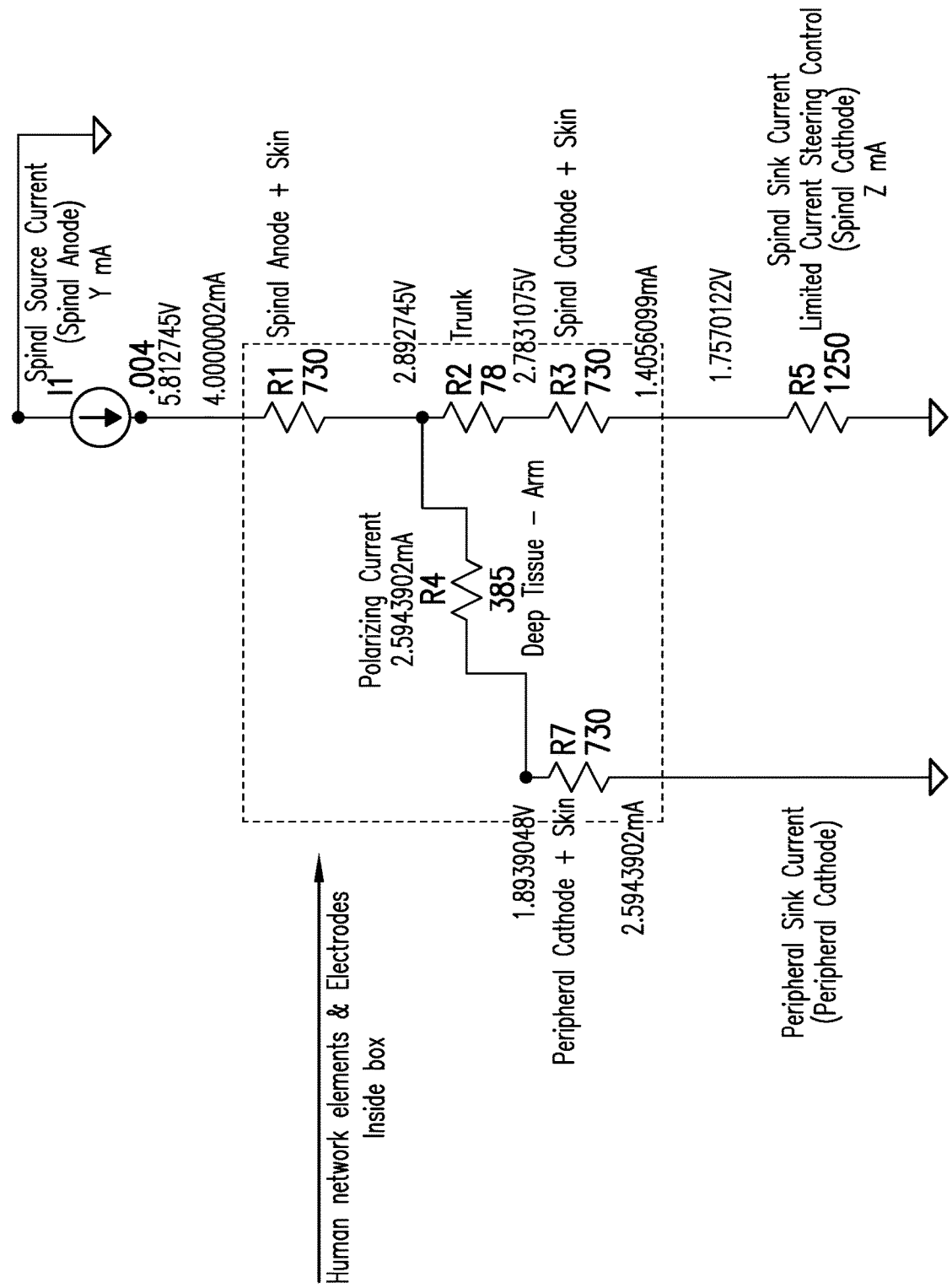

METHOD AND APPARATUS FOR CONTROLLING MULTI-SITE NEUROSTIMULATION

CROSS-REFERENCE TO RELATED APPLICATIONS

Priority is claimed upon U.S. Provisional Application Ser. No. 62/748,684, filed Oct. 22, 2018, entitled: Method And Apparatus For Multi-Site Neurostimulation For Treatment Of Spasticity, incorporated herein by reference in its entirety for all purposes whatsoever.

FIELD

The present invention relates to method and apparatus for modulating spinal cord excitability for treatment of neurological disorders.

DESCRIPTION OF RELATED ART

The neurostimulation system described in U.S. Pat. No. 9,283,391, incorporated herein by reference for all purposes whatsoever, teaches multi-site neurostimulation for improving performance of a target effector organ, including applying direct current to a spinal location associated with efferent neural outflow to a target effector organ, e.g., to a muscle, combined with applying direct current to a peripheral location associated with control of the target. Such patent teaches systems pairing trans-spinal direct current stimulation of the spinal cord (tsDCS) with direct current stimulation of the peripheral nerve (pDCS) leading to a target body part, e.g., to an effector organ such as an afflicted muscle.

The spinal electrode (as spinal anode) is placed over the spinal column at the level of the spinal outflow to the target muscle of interest, while the spinal return (as spinal cathode) is placed at a non-spinal location, e.g., over the abdomen or a bony location or the like. For the peripheral stimulation, peripheral anode and cathode electrodes are placed over a section of the descending nerve, proximal to the location of the muscle of interest. The system current is adjusted at a power source and applied to the spinal circuit and is further split into the peripheral circuit according to the resistance setting of a variable resistive control. However, the adjustment of the peripheral circuit will reduce or increase the current in the spinal circuit, and which will be subject to fluctuation as the impedance/resistance within the various electrode interfaces and tissue pathways of the applied treatment system vary during a treatment session.

Notwithstanding the utility of such device, more precise current control is desired for improved operation. More specifically, there remains a need for improved real-time control of the current flow between respective electrodes as such are applied to the patient for delivering and maintaining therapeutic currents during multi-site neurostimulation, as will accommodate real-time variations in the various circuit pathways during treatment. The present invention overcomes this instability and provides improved real-time current control.

BRIEF SUMMARY OF THE INVENTION

Improved method and apparatus for neuromodulation and regulation of effector organs are disclosed herein. In one or more embodiments, the system of these teachings includes a stimulation component configured to provide spinal direct current stimulation associated with modulation of a target effector organ and a stimulation component configured to provide stimulation of a nerve associated with the target effector organ. An illustrative embodiment, the system of these teachings includes a controller component configured to control various stimulation currents, as more particularly set forth in several illustrative embodiments.

In the present invention, implementation of current steering and current control provides improved delivery and maintenance of the currents in a multi-site neuromodulation system during treatment of a patient for a neural indication. Aspects of the present invention provide more precision and better current control in a neuromodulation system, featuring improved steering of electrical current for improved control of intended neurostimulation treatment. In one illustrative embodiment, a system is provided to operate fully independent of the time-varying loads at the electrode skin interfaces and in the patient's neural pathways connecting between system electrodes.

In illustrative embodiments, a multi-site neurostimulation system features versions of pairing trans-spinal direct current stimulation of the spinal cord (tsDCS) with direct current stimulation of the peripheral nerve (pDCS) leading to a target body part, e.g., to an afflicted muscle, with improved control of the currents delivered by the stimulation circuits.

In various embodiments we overcome the real-world difficulties in crossing the skin barrier with applied current and in responding to changes in tissue conductance, while providing a stable and well-controlled stimulation environment. In an illustrative embodiment, the present invention provides and maintains adaptive current stimulation with effective control of the currents delivered by multiple stimulation circuits.

More specifically, it has been found that quality of performance requires a responsive current control mechanism able to accommodate simultaneously the various local time-varying resistance/impedance changes occurring during the stimulation session at multiple system locations within the operating system. These system locations include both the active skin-surface interface of the system electrodes and also the active spinal, peripheral and polarization neural pathways. This active accommodation provides better current control at the essential spinal and polarizing current paths for improved stimulation control.

In one aspect we provide a system based on DC neurostimulation, including trans-spinal direct current stimulation at a spinal cord location associated with control of the target body part, and direct current stimulation of the peripheral nerve associated with the afflicted target body part, e.g., a muscle, controlling the power source supplying the neuromodulation device and providing controlled flows of direct current in spinal, peripheral and polarization circuits.

Illustrative embodiments of the neurostimulation system 50 of the invention pass low level direct current through the body to achieve certain therapeutic effects for patients having certain medical conditions. Versions of the three circuits, spinal, peripheral and polarization, are disclosed availing improved safety and performance. In one embodiment this includes providing resistive control in one leg of one of these circuits, including resistive current control in the low voltage spinal (return) side of the spinal circuit, with current split between polarization and spinal circuits 65/35%, ranging about +/−10%.

In one illustrative embodiment, the system provides for constant current control that enables operation fully independent of the time-varying loads at the electrode skin interfaces and in the patient's neural pathways connecting between system electrodes. In other illustrative embodiments we replace the resistive control with dynamic current control at the spinal anode in a three electrode embodiment, and at the spinal anode and at the peripheral anode in a four electrode embodiment. In another embodiment, constant current nodes are provided at the peripheral and at the spinal current source and at the spinal cathode (acting in place of a steering resistor), while the peripheral cathode action follows as it is determined by the control of the peripheral and spinal anodes and spinal cathode. In one illustrative embodiment, the system provides for constant current control that enables operation fully independent of the time-varying loads at the electrode skin interfaces and in the patient's neural pathways connecting between system electrodes.

In another illustrative embodiment, the system measures the current through both the spinal and peripheral anodes in real time and presents it on a front panel display. Thereafter polarizing current and the spinal cathode current are metered or are calculated and displayed.

In another illustrative embodiment we provide highly precise current control featuring three constant current sources applied variously to the spinal, polarizing and peripheral circuits. Constant current sources (sinks) are placed as follows: One source in series on the "high" side of the spinal circuit, one source in series on the "high" side of the peripheral circuit and one sink in series on the "low" side of the spinal circuit in a four electrode configuration. This embodiment successfully maintains predetermined currents, and current ratios, as the electrode/skin impedance and body impedance vary over the course of a treatment.

In a simplified embodiment, the "low" side current sink in the spinal circuit is replaced with a resistor to steer a greater portion of the spinal current to the polarizing circuit but does not maintain the precision of current rations due to changing electrode/skin impedances.

Embodiments of these teachings enable regulation of effector organs, such as for treatment of muscle tone for control of spasticity at a target muscle. In embodiments of these teachings utilizing implantable electrodes, wearable or implantable stimulation devices may be employed. For certain applications, administration of tsDCS therapy for disorders at effector organs will be sufficient if done between several times a week for a number of sessions on an outpatient basis.

For some patients, treatment on such a schedule will be insufficient. Constant application of tsDCS, or application for several hours or sessions per day, for practical beneficial effects, may be indicated. This can be assisted by enabling mobile delivery of such therapy. For such applications, embodiments of the present teachings are understood as a wearable device or implantable device. Such devices are compact versions of these teachings. In one embodiment, the device footprint is shrunk to the approximate diameter of a silver dollar, and is attached to the skin surface of the spine with adhesive mounting, implanted magnets, or other methodologies. Preprogramming of microprocessor/memory provides the capability to accommodate such long-term treatment, with adequate internal monitoring.

In several embodiments of the present invention anodal trans-spinal DC stimulation with current steering is implemented with a resistor R in series with the spinal cathode. The ratio of the split of spinal source current at spinal anode is controlled by resistor R. In an embodiment this is practiced with a single constant current source. Current is metered in series with the peripheral cathode.

In additional embodiments of anodal trans-spinal DC stimulation with current steering is implemented by spinal sink current in series with the spinal cathode and the ratio of spinal source current split is controlled and maintained via the spinal sink current. Other embodiments feature combinations of current sources and electrode configurations including low side or high side current control.

In further embodiment of the invention we provide a DC neurostimulation system for providing trans-spinal direct current stimulation at a spinal cord location associated with control of a target body part of a sentient being, and direct current stimulation of the peripheral nerve associated with control of the target body part, configured to deliver stimulation via electrodes at skin interfaces, having a stimulation component configured to provide spinal direct current stimulation associated with modulation the target effector organ; a stimulation component configured to provide stimulation of the peripheral nerve associated with the target effector organ; said components supplying controlled flows of direct current in spinal, peripheral and polarization circuits, and a controller component having a power source for supplying controlled flows of direct current in the spinal, peripheral and polarization circuits to provide stimulation currents to the spinal and peripheral locations associated with control of the target body part, the controller component configured to control the stimulation currents and to provide current steering and current control to the currents at the peripheral and spinal locations. Embodiments further include: a power source and the controller configured to provide said current independent of time-varying loads at the electrode skin interfaces and in the patient's neural pathways connecting between system electrodes; and providing resistive current control in the low voltage spinal return side of the spinal circuit, with current split between polarization and spinal circuits approximately 65/35%+/−10%; and utilizing one of the set of varying, pulsed and constant current DC.

In further embodiment of the invention we provide the system having a power source supplying controlled flows of direct current in spinal and polarization circuits, providing dynamic current control at the spinal anode and at the spinal cathode in a three electrode embodiment, at the spinal anode, at the spinal cathode and at the peripheral anode, without the need for resistive current splitting; and the system having a power source supplying controlled flows of direct current in spinal and polarization circuits, providing dynamic current control at the spinal anode and at the spinal cathode in a four electrode embodiment, without the need for resistive current splitting; and the system with pairing trans-spinal direct current stimulation of the spinal cord (tsDCS) with direct current stimulation of the peripheral nerve (pDCS) leading to the target body part, wherein the controller is further configured to pass low level direct current through the body to achieve therapeutic effects for patients having neurologic conditions, wherein in a further embodiment of the invention provides three circuits, spinal, peripheral and polarization, and further configured to provide resistive control in one leg of one of these circuits with current split between polarization and spinal circuits 65/35%, ranging about +/−10%, which may control resistive current control in the low voltage spinal (return) side of the spinal circuit.

In further embodiment of the invention the controller is configured to provide constant current control independent of the time-varying loads at the electrode skin interfaces and in the patient's neural pathways connecting between system electrodes, and in another embodiment the controller is further configured to provide dynamic current control at at least one of the spinal anode in a three electrode embodiment and at the spinal anode and at the peripheral anode in a four electrode embodiment.

In another embodiment, the controller is configured to provide constant current nodes at the peripheral current source and at the spinal current source and at the spinal cathode, wherein the peripheral cathode action follows as it is determined by the control of the peripheral and spinal anodes and spinal cathode; and wherein the controller is further configured to measure current through both the spinal and peripheral anodes in real time, and the polarizing current and the spinal cathode current are one of the set of metered and calculated.

In another embodiment, the controller is further configured to provide three constant current sources variously to the spinal, polarizing and peripheral circuits, wherein constant current source sinks are placed as follows: one source in series on the "high" side of the spinal circuit, one source in series on the "high" side of the peripheral circuit, and one sink in series on the "low" side of the spinal circuit, in a four electrode configuration; and further configured to provide three constant current sources variously to the spinal, polarizing and peripheral circuits, wherein constant current source sinks are placed as follows: one source in series on the "high" side of the spinal circuit, one source in series on the "high" side of the peripheral circuit, and one sink in series on the "low" side of the spinal circuit, in a four electrode configuration, wherein the "low" side current sink in the spinal circuit is replaced with a resistor to steer a greater portion of the spinal current to the polarizing circuit.

In a method of the invention for operating a DC neurostimulation system for providing trans-spinal direct current stimulation at a spinal cord location associated with control of a target body part, and direct current stimulation of the peripheral nerve associated with control of a target body part, with a power source supplying controlled flows of direct current in spinal, peripheral and resulting polarization circuits, comprising the step of splitting current between the polarization and spinal circuits approximately 65/35%+/−10%; in one embodiment, further supplying the neuromodulation device and controlled flows of direct current in spinal and polarization circuits and providing dynamic current control at the spinal anode and at the spinal cathode in a three electrode embodiment and at the spinal anode, at the spinal cathode and at the peripheral anode in a four electrode embodiment; in another embodiment, wherein the system is configured for utilizing one of the set of pulsed constant current DC monopolar and constant current DC biphasic, and providing a plurality of spinal and peripheral electrodes, both anode and cathode, each electrode in series with its own constant current source for further refinement of current focality across the spinal cord and peripheral nerve, further including one of wherein the activation of the electrodes may vary with time producing a dynamic focality pattern and wherein array of small electrodes each with its own constant current source enable finely defining current paths across the spine. In a further embodiment, the method further includes the step of implementing control algorithms from the set including:

a: in the case where we source X mA peripheral source current through the peripheral anode 28 and Y mA spinal source current through the spinal anode and we sink Z mA spinal current through the spinal cathode, to can control Z mA through the sink electrode and, therefore, the sink current through the peripheral cathode is X+Y−Z; and b: wherein three current sources represented by G4, G5, and G6 are transconductance amplifiers, and the control signals to G4, G5 and G6 are I_SPINE, I_PERI and I_STEERING respectively, which signals are voltages from a system digital to analog converter (DAC) which, in turn, receives a control digital value from the system microprocessor, wherein the microprocessor implements algorithms for calculating the desired Spinal Source Current, Peripheral Source Current and Spinal Sink Current (for current steering), wherein the current sources G4 and G5 need to be high voltage compliance to overcome the initial high impedances of the electrode-skin interface, with high voltage supplied by V2; and c: wherein with the 'High Side' transconductance amplifiers G4 and G5, I_COMMAND is a generic voltage input represented by I_SPINE and I_PERI; and PROGRAMMED_I is the resulting current, having high voltage compliance; and d: wherein in a circuit embodiment of 'low Side' transconductance amplifier G6, I_COMMAND is a generic voltage input represented by I_STEERING, and PROGRAMMED_I is the resulting current, for controlling currents returning to common through a cathode; and e: wherein Z is a function of Y so that Z=a*Y where a is typically between 0.2 and 0.8, and where there is a need to control one sink with a*Y or the other with ((1−a)*Y)+X; and f: wherein Z is a function of X and Y so that Z=a*(X+Y) is typically between 0.2 and 0.8, and where there is a need to control one sink with a*(X+Y) or the other with (1−a)*(X+Y); and g: where X and Y are functions of time, X(t) and Y(t) and Z is also a function of time. and 'a' may also be a function of time and the time functions may be pulsed constant current DC monophasic, pulsed constant current charge balanced biphasic, pulsed constant current charge imbalanced biphasic and pulsed constant current balanced biphasic with interphase delay; and h: further including the step wherein where X and Y and Z may be influenced by other conditions such as a feedback device to sense force, temperature, or vital signs from the human body, and wherein X and Y and Z are controlled by a function that monitors voltage to minimize discomfort or any noted hazardous condition.

These and other embodiment are set forth below

BRIEF DESCRIPTION OF THE DRAWINGS

The present illustrative and further embodiments are described in conjunction with the following figures, where specifically numbered components are described and will be applicable to various configurations of the disclosure.

FIG. 4A illustrates anodal trans-spinal DC stimulation in an embodiment of the invention with a single constant current source and current steeling is implemented by resistor R in series with the spinal cathode, wherein the ratio of spinal source current split between the spinal and polarization pathways is controlled by R.

DETAILED DESCRIPTION

Definitions

Figure 1:
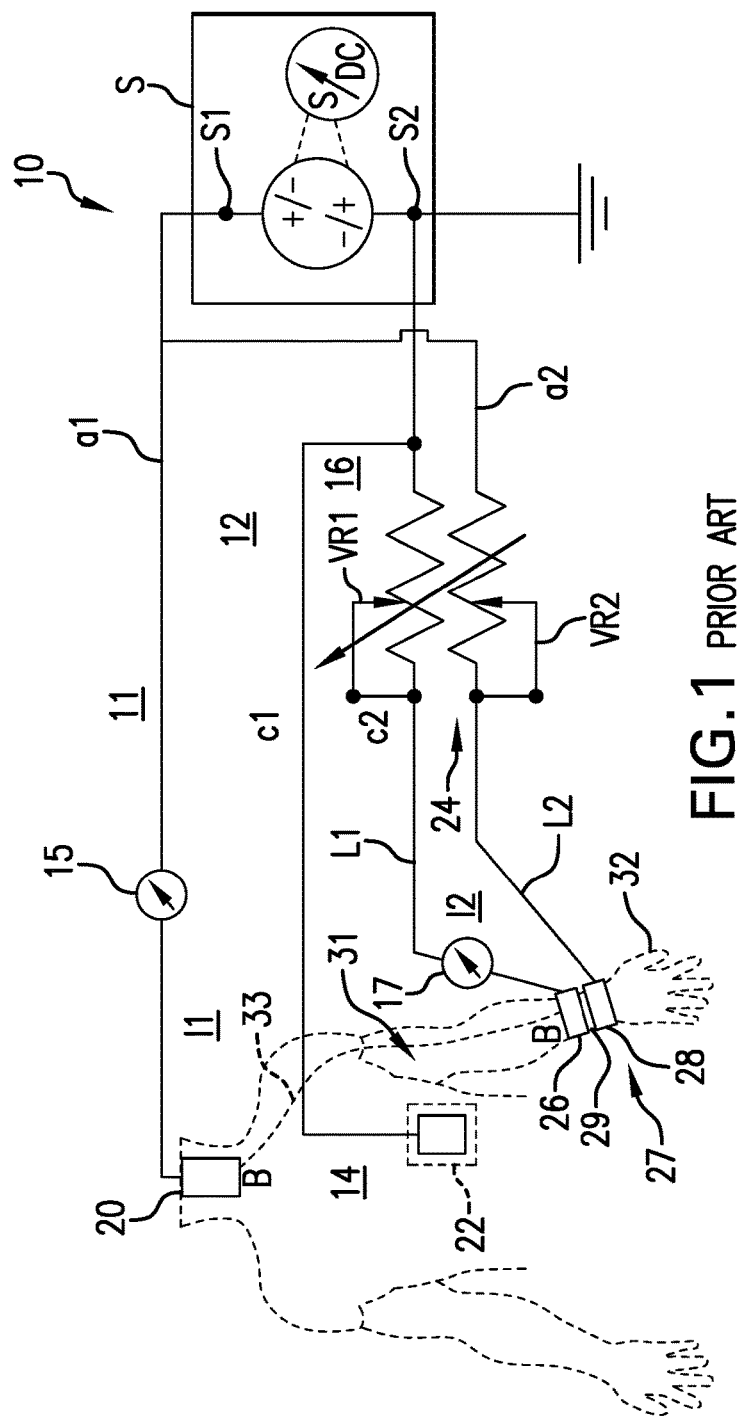
FIGS. 1 and 2 are based upon the prior art multi-site neurostimulation stimulation device 10of U.S. Pat. No. 9,283,391.

The following definitions pertain to the present disclosure, with the understanding that such may be modified by context of use. For purposes of the teaching of the present teachings:

As used herein, the singular forms "a," "an," and "the" include the plural reference unless the context clearly dictates otherwise.

The terms "nerve" or "neuron" may be referred to herein as including nerves, neurons, motor neurons and interneurons and the like, and are generally referred to herein as "nerve(s)" or "neuron(s)";

The terms "nerve stimulation" and "neural stimulation" are used interchangeably to describe applications of the present teachings;

The terms "neuromodulation," "modulation," "stimulation" and "regulation" are used interchangeably for purposes of this disclosure and indicate an effect imposed upon a target in practice of the present teachings;

The terms "dysfunction," "disorder," "defect" and "abnormality" are used interchangeably for purposes of this disclosure and indicate the concept of medically recognized conditions suitable for medical intervention:

The term "effector organ" refers to a neurally enervated organ that produces an effect in response to nerve stimulation. Muscles are included within such definition for purposes of this disclosure. The effects of stimulation of the present teachings upon an effector organ or muscle are discussed interchangeably for purposes of the present teachings.

The term "electrical stimulation," as used here in refers to the production or introduction of current into spinal nerve, neuron, circuit or pathway, whether by applying a voltage or magnetically inducing a current, for either excitation or inhibition of nerve fibers, also referred to as up-regulation or down-regulation.

The present disclosure teaches applications of trans-spinal direct current stimulation to affect muscle tone by modulating spinal cord excitability and is applied in treatment of living beings, in both human and veterinary applications. Practices of the present teachings treat hypertonic or hypotonic conditions. In one illustrative practice of the present teachings, we treat a spastic hand in patients having spastic cerebral palsy, by down-regulation of high muscle tone. In another practice, we treat weak muscles such as at lower limbs in patients with Down's syndrome, by up-regulation of muscle tone. These are examples by way of illustration and not by way of limitation of the scope of these teachings.

In one or more embodiments, the system of these teachings includes a stimulation component configured to provide stimulation of a nerve associated with a target effector organ and a second stimulation component configured to provide spinal direct current stimulation associated with modulation of the target effector organ. An illustrative embodiment, the system of these teachings includes a power source and controller component configured to control various stimulation currents, as more particularly set forth in several illustrative embodiments.

Figure 2:
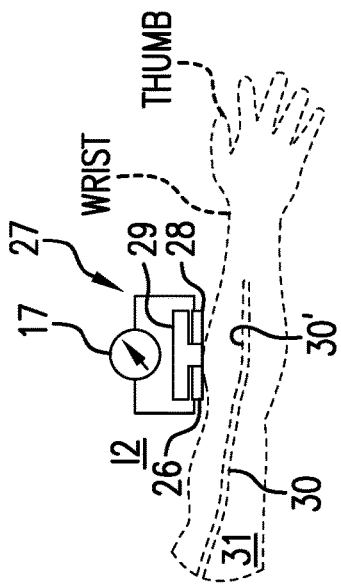

The present invention improves upon the teachings of the '391 patent, which teaches in FIGS. 1 and 2 an effector organ regulating device 10 having a tsDCS-pDCS stimulation circuit for modulating spinal cord excitability, driven by a variable constant DC source S. Depending upon desired direction of current flow, the respective current sources S1 and S2 are positive or negative. For a muscle tone down-regulating configuration of device 10, source S1 and the spinal electrode 20 are positive, and source S2 and proximal distal nerve electrode 26 are negative. For an up-regulating configuration of the device, power source S is switched accordingly to apply S1 negative and S2 positive.

FIGS. 1 and 2 illustrate an example of regulation of the median nerve for resolving a chronic fisted hand and fingers with high muscle tone. The stimulation circuit 11 has a spinal branch 12 for supplying sub-threshold stimulation to the spinal cord 14 at a first current level I1 and has a neural branch 16 for supplying to the nerve of interest (e.g., median nerve) sub-threshold stimulation at a second current level I2.

In one illustrative embodiment, when setting up for treatment, the current I2 is brought up to measurable EMG and then reduced to subthreshold (no apparent nerve activity). Meanwhile, spinal DC is always subthreshold because of its low intensity (about 2 to 4 mA) when applied on the surface of the skin.

FIG. 1 shows the spinal branch 12 with spinal electrode 20 positioned at a spinal enlargement of spinal cord 14. In some embodiments, the location of electrode 20 is at the cervical enlargement for upper limb muscles to be treated and at the lumbar enlargement for lower limb muscles to be treated, as will be appreciated by a person skilled in the art. For treatment of hand and fingers, it is at the cervical enlargement behind electrode 20 in FIG. 1. The spinal reference electrode 22 is positioned on an anterior location, such as the abdomen.

In FIG. 1, current in neural branch 16 is controlled via a variable resistance circuit 24, which may include one or more variable resistors, e.g., VR1 and VR2. The peripheral circuit includes electrodes 26, 28 mounted over nerve 30 at a local nerve segment 30', in this example on median nerve 30 of arm 31, shown in FIG. 2.

The spinal electrodes 20, 22 are part of a stimulation circuit 12 for applying trans-spinal direct current stimulation (tsDCS) to the spine 14 and the second pair of electrodes 26, 28 are part of a peripheral stimulation circuit 16 for applying stimulation (pDCS) to nerve 30 associated with the target body part. In turn, these two circuits, spinal and peripheral, cooperate to define a resulting polarization circuit 33 between respective anodal electrode 20 of the spinal circuit 12 and cathodal electrode 26 of the neural circuit 16. The resulting polarization circuit 33 stimulates the captured target descending neuron 30 and achieves a desired regulation of excitability of effected spinal motoneurons and interneurons that enables the desired outcome of regulation of muscle tone. The tsDCS is applied between the two electrodes/poles, 20, 26, to polarize the neuron between the two electrodes. Also in this embodiment, the peripheral circuit 16 is located at and polarizes the local segment 30' of descending nerve 30 associated with control of the target body part (arm/hand). The proximal and distal electrodes 26, 28 (i.e., two poles) of this neural peripheral circuit 16 are arrayed over the target nerve segment 30'. This peripheral stimulation circuit 16 can be applied to locations in many parts of the body and the character of stimulation energy will be selected accordingly. In a muscle tone treatment embodiment, peripheral direct current stimulation (pDCS) is applied between electrodes 26, 28 for polarization of femoral nerve section 30', while the cathodal peripheral electrode 26 also provides the cathode of the polarization circuit 33.

Down regulation and up regulation of muscle tone are guided by the direction of current flow arising from interaction between the adjacent electrodes 20, 26 of the spinal and neural circuits 12, 16 that define the polarization circuit 33. In one embodiment, For down-regulation, the spinal electrode 20 is anodal and proximal peripheral nerve electrode 26 is cathodal. This defines the needed spine-to-nerve polarization circuit 33 (polarizing current flow path 30) between these two energized electrodes of the two polar circuits 12, 16. For up-regulation, the proximal nerve electrode 26 is anodal and the spinal electrode cathodal. This defines the current flow direction of the nerve-to-spine polarization circuit 33 (polarizing current flow path) between these two energized electrodes.

In one illustrative use of system of FIGS. 1-2, the electrodes of regulation device 10 are attached to the subject and the spinal circuit is properly set. An electromyography (EMG) device 32 is connected to monitor increased stimulation at the muscle of interest associated with the nerve as stimulated by the current flow. As will be appreciated by a person skilled in the art, in the present example of the median nerve stimulation, the EMG was attached across the thumb to measure action potential at the abductor pollicis brevis muscle (on the palm side of the hand). The pre-treatment clenched fist and EMG attachment at the thumb is indicated in FIG. 1 and FIG. 2. Post-treatment, spasticity was reduced as the hand and thumb were now relaxed and extendable, and no longer clenched.

In practice of the present invention, we have recognized that there is substantial variability from patient to patient and time to time as to skin surface resistance and system conductance as applied to the torso. Resistances can change at a particular electrode or anywhere along the several neural paths, i.e., the spinal path of the spinal circuit 12, from spinal anode 20 to spinal cathode 22, or the peripheral path of the peripheral circuit 16, from peripheral anode 28 to peripheral cathode 26, or the polization path of the resulting polarization circuit 33, defined along the descending neuron of interest 30 between the spinal anode 20 and the peripheral cathode 26.

In the following teachings, we improve upon delivery of treatment in the prior art while achieving and maintaining, during a full treatment session, such as for down-regulation of spasticity, a ratio of current between the polarization circuit and the spinal circuit of about 65% polarization current (anode 20 to cathode 26) to 35% spinal current (anode 20 to cathode 22). We have found that this provides a favorable stimulation condition for successful functional use.

Figure 3:
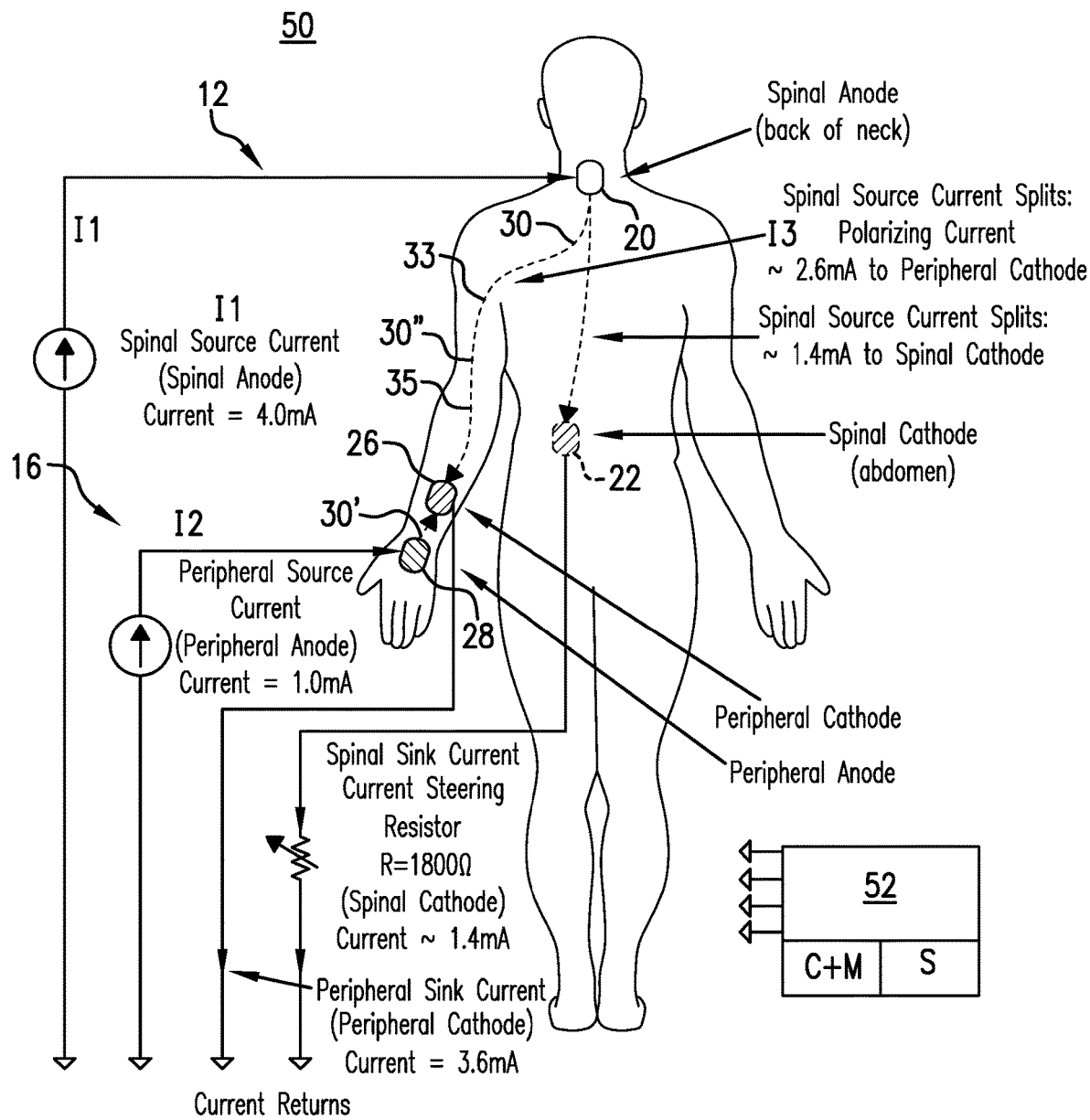
FIG. 3 illustrates an embodiment of the present invention wherein anodal trans-spinal DC stimulation with current steering is shown implemented by resistor R in series with the spinal cathode, for controlling the ratio of the split spinal source current.
Figure 4:
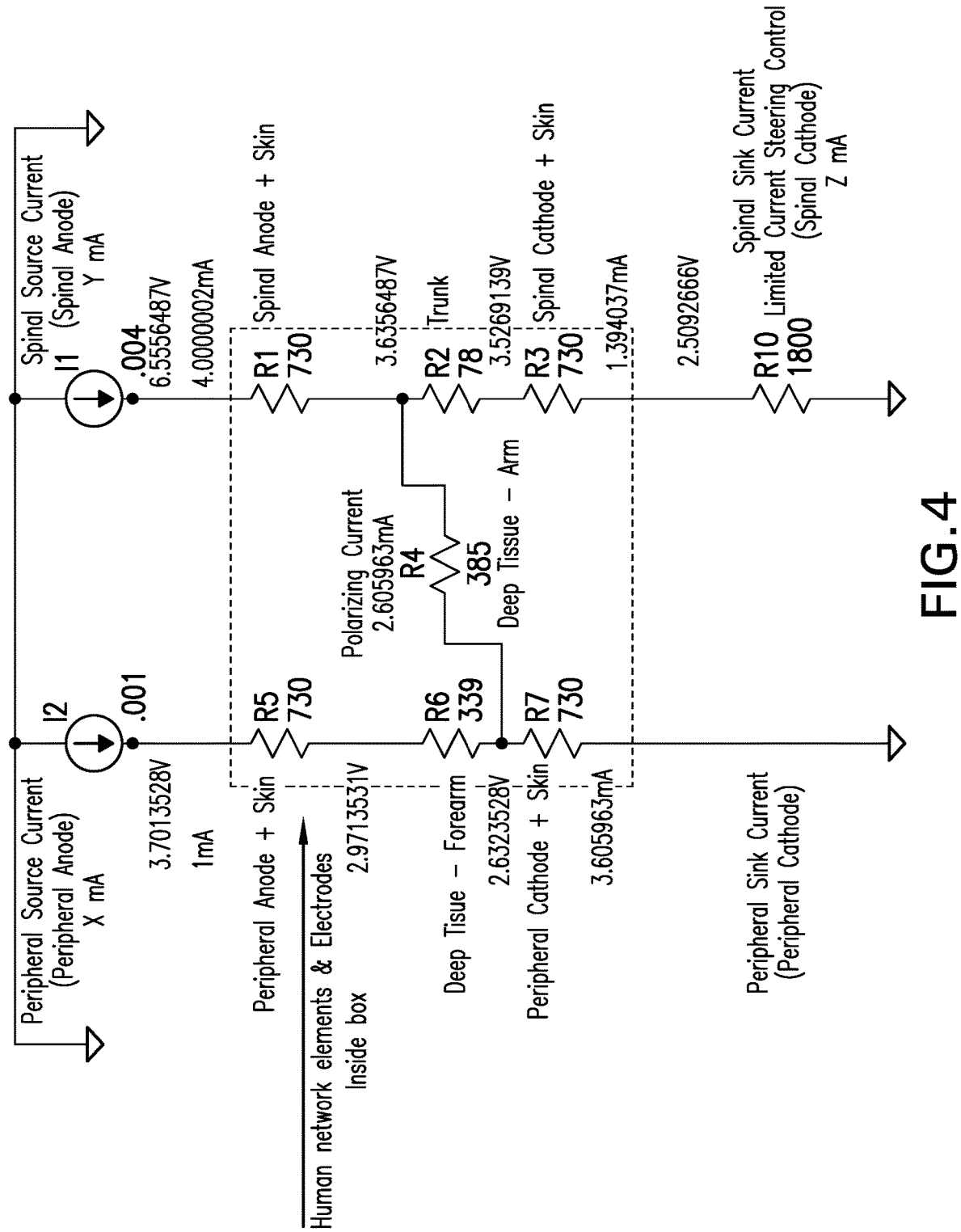
FIG. 4 illustrates anodal trans-spinal DC stimulation in an embodiment of the invention wherein current steering is implemented by resistor R in series with the spinal cathode, wherein the ratio of the spinal source current split between the spinal and polarization pathways is controlled by R.

In one embodiment of the invention, referring to the system of stimulator 50 shown in FIG. 3 and to the stimulation circuit analysis of FIG. 4, we illustrate an embodiment for treatment of spasticity by implementing low-side resistive current control in the spinal circuit 12, and then employing two constant current sources, (e.g., 4 mA and 1 mA), for assuring controlled delivery of desired polarization current flow from spinal anode 20 to peripheral cathode 26, for treatment of spasticity. This overcomes excessive variability in the unregulated device of FIGS. 1-2 of the prior art.

In an illustrative system 50 of the invention for reduction of spasticity, respective constant currents are applied at anodal spinal circuit 12 and peripheral circuit 16, with a resulting polarization circuit 33 defining a polarization path formed along the descending neuron of interest 30 which is energized between spinal anode 20 and peripheral cathode 26. The current-steering series resistor R is implemented with system current metered on the low voltage side of the spinal circuit. In the illustrative embodiment of FIG. 3, anodal trans-spinal DC stimulation is shown with current steering implemented by resistor, R, in series with the spinal cathode 22. The ratio of the split of spinal source current at spinal anode is controlled by R.

In an illustrative embodiment of stimulator 50, various electrodes are attached via I/O components to a controller 52. A power source S is either internal or external. Controller 52 preferably includes a computer C with microprocessor/memory M and has a user control interface, which may include a conventional touch screen. The polarities are established for desired down-regulation or up-regulation in combination upon control of the DC power source S by controller 52, for supplying and driving the system circuits.

Controller 52 assures that the desired interactive polarization circuit 33 is properly formed between electrodes located according to these teachings. In one illustrative embodiment, the administrator enters data at the data input to the system and the controller fixes spinal and neural electrode polarities and signal levels according to entered data, which may include patient body type (e.g., small, medium, large) and treatment mode (e.g., up or down regulation of the target organ). Accordingly, the administrator affixes the spinal electrode 20 at the appropriate spinal location and a related reference electrode 22 at a non-spinal return location, and affixes at least one peripheral electrode 26 at the target peripheral location to at least define the desired polarization segment 30" of the descending spinal neuron 30 in a three electrode system and in a four electrode system affixes a second peripheral electrode to further define a peripheral nerve segment 30' at the target location.

In the illustration of FIGS. 3 and 4, there are two constant current sources, one source SI1 for the spinal current I1 and one source SI2 for the peripheral current I2. In an embodiment applying 4mA stimulation between the spinal electrodes 20, 22 and peripheral electrodes 26, 28, having a two electrode spinal circuit 12 and a two electrode peripheral circuit 16, we find that a current steering resistor in the neighborhood of 1.8 k ohm (FIG. 3: R=1800Ω; FIG. 4: R10=1800Ω) provides a favorable current balance between the polarization and spinal current that enables successful treatment in a four electrode multi-site neurostimulation stimulation circuit of system stimulator 50.

With reference to the prior art of FIG. 1, we replace the variable VR1/VR2 with a resistor, whether fixed or variable, set at or about 1.8 k ohm, as shown in FIG. 3. This adaptive embodiment is configured for varying the ratio between the spinal current I1 and the polarization current I3, and not for varying the ratio of spinal current I1 to peripheral current I2 as configured in FIG. 1. Controlling the ratio of spinal current relative the current I3 of the critical polization path 33 provides a more meaningful control mechanism for application of treatment in view of the variable conditions of the human patient during treatment.

It will be appreciated that this configuration provides current control of the three circuits: the spinal circuit 12 established between the spinal anode and the spinal cathode; the peripheral circuit 16 established between the peripheral anode and the peripheral cathode; and the polarizing circuit 33 creating a key polarization path 35 defined by the nerve portion 30" of descending neuron 30 between the spinal anode 20 and the peripheral cathode 26. The spinal circuit cathode 22 and peripheral circuit cathode 26 return to the same electrical common. The resistor in series with the spinal cathode 22 controls the splitting of the current from the spinal anode to both the polarizing circuit 33 and the spinal circuit 12.

In one illustrative embodiment, 4 mA spinal source current of the spinal circuit 12 applied at the spinal anode 20 is split 1.4 mA to the spinal cathode 22, sunk through resistor R at the spinal cathode, and 2.6 mA split to the peripheral cathode 26 of the peripheral circuit 16. The peripheral current source PS of the peripheral circuit supplies 1 mA current to the peripheral anode 28 while 3.6 mA is sunk via the peripheral cathode 26. The 1.0 mA is applied to peripheral circuit to engage the local neural process at the target segment of the peripheral nerve between peripheral anode 26 and peripheral cathode 28, and 4 mA is applied at the spinal anode 20, and with the added 1.8 k ohm resistance R (combined with the anticipated skin-surface and tissue impedances of the patient) this splits the applied 4 mA, with 2.6 mA sinked along the polarization path 33 spinal anode to peripheral cathode 26, and 1.4 mA sinked at the spinal low side from the spinal cathode. The spinal anode to peripheral cathode current flow polarizes the descending medial nerve serving the muscle(s) such as affecting a spastic wrist. The peripheral cathode sinks the 2.6 mA of the polarization circuit and also the 1.0 mA of the peripheral circuit applied at the peripheral anode.

We have discovered that, on average, low side resistance of 1.8 k ohms adequately splits the applied spinal current (4.0 mA in the illustration of FIG. 3) with approximately 65% of the 4.0 mA delivered from the spinal anode through the polarizing path 35 to the peripheral cathode (polarization circuit 33) and back to the power source S, and approximately 35% of the 4.0 mA delivered by the spinal anode 20 across the spinal cord (spinal circuit 12) to the spinal return electrode and back to the power source.

We have found that this combination enables successful treatment of spasticity in system 50 in an average adult patient, preferably splitting the current 65% along the polarized segment 30" of neuron 30 between spinal anode 20 and peripheral cathode 26, and with 35% in the spinal circuit 12, spinal anode 20 to spinal cathode 22, provides favorable therapy in a spastic patient. This 1.8 k ohm current-steering enables a desirable split of current in this system. However, in one embodiment, it is possible, under user control, to vary this 65/35% split by about 10-20% or so, in practice of the invention to accommodate special treatment conditions.

In an illustrative embodiment we provide superior control by incorporating three constant current sources in a system having spinal 12, polarization 33 and peripheral circuits 16. The constant current sources (sinks) are placed as follows: One source in series on the "high" side of the spinal circuit, one source in series on the "high" side of the peripheral circuit and one sink in series on the "low" side of the spinal circuit in a four electrode configuration. This embodiment is for maintaining both predetermined currents, and current ratios, even as the electrode/skin impedance and body impedance vary over the course of a treatment.

In another embodiment, the "low" side current sink in the spinal circuit is replaced with a resistor to steer a greater portion of the spinal current to the polarizing circuit but does not maintain the precision of current rations due to changing electrode/skin impedances. Other embodiments include combinations of current sources and electrode configurations as described below.

In a further illustrative embodiment, in order to accommodate treatment of a wider range of patients by a skilled user, implementation includes a variable resistor, as indicated in FIGS. 3 and 4, now ranging from about 1-3 k Ohm. This would enable substantial range of current adjustment for a wide range of body types and treatment needs. The current metered on the peripheral low side enables real-time adjustment of this spinal current flow, for monitoring of change in the current split, and this in turn results in real-time adjustment of the delivered polarization current.

It will therefore be appreciated that in FIGS. 3-4, the spinal circuit with low side series resistance is for splitting of current at the anode of the spinal circuit between both i) the cathode of the spinal circuit and ii) the cathode of the peripheral circuit. The low voltage side of the spinal circuit sets the level of polarization current flowing down the neural pathway defined between spinal anode and peripheral cathode, which is balanced against the remaining system impedances of the neural pathways of the operating stimulator 50.

Figure 3A:
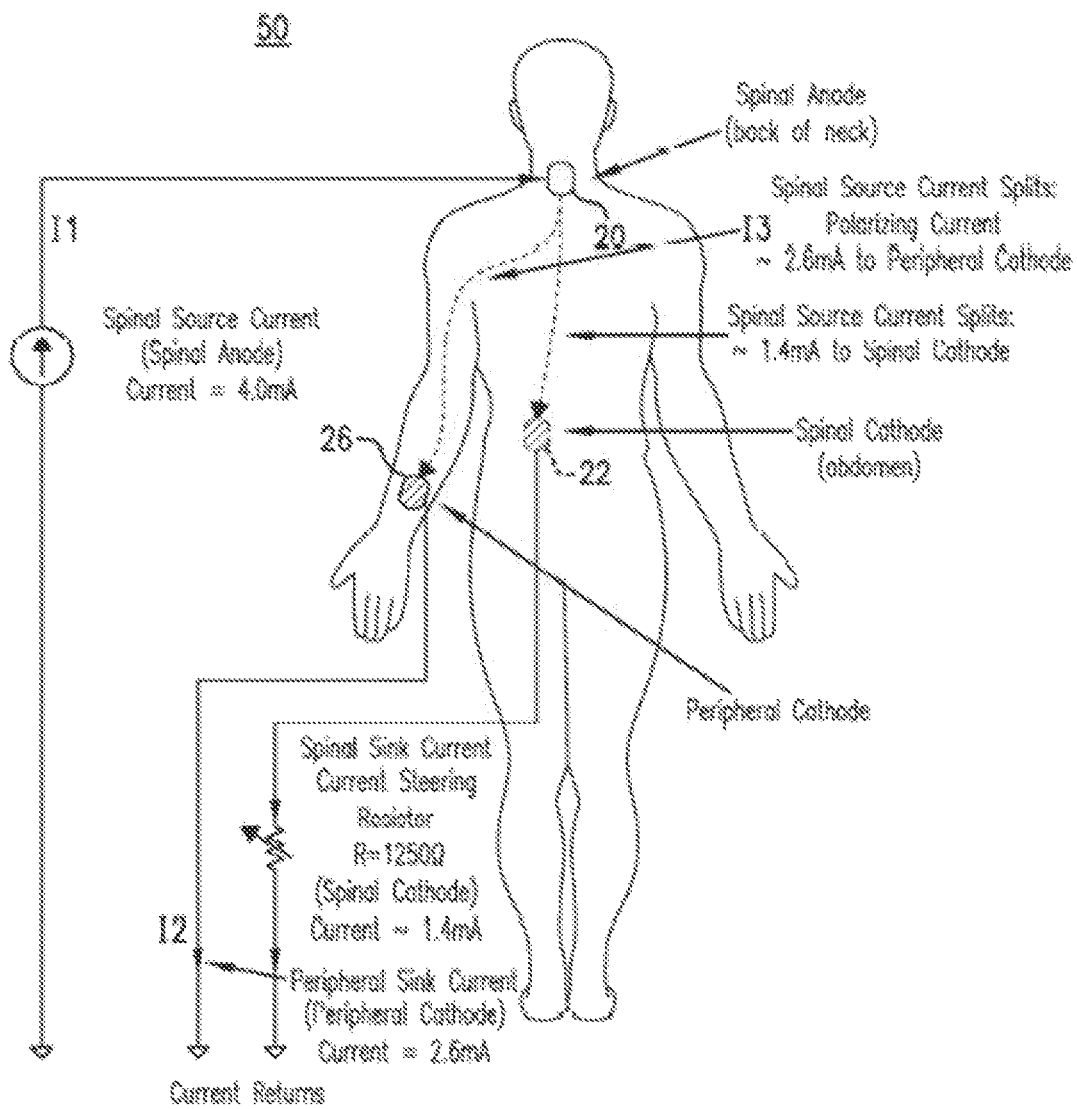
FIG. 3A illustrates an anodal trans-spinal DC stimulation with a single constant current source embodiment of the invention. Current steering is implemented by resistor R in series with the spinal cathode, where the ratio of spinal source current split is controlled by R.

In the case of a simplified device of the invention illustrated in FIGS. 3A and 4A, the peripheral constant current I2 and the peripheral anode 28 are eliminated, dispensing with the local direct stimulation of the peripheral nerve segment 30' of the target muscle. Now a single constant current I1 source addresses circuit changes of the entire circuit, albeit without the precision of the circuit of FIGS. 3 and 4. In FIG. 3A, the anodal stimulation with a single constant current source provides current steering by resistor, R, in series with the spinal cathode. The ratio of spinal source current split is controlled by R. Current is metered in series with the peripheral cathode.

The simplified configuration of FIGS. 3A and 4A still sets up two stimulation circuits: a spinal circuit 12, with spinal anode 20 and non-spinal cathode 22, placing anode 20 at a spinal location at a target spinal neuron(s) associated with control of a target body part, and a peripheral circuit 16 at peripheral cathode 26 positioned on the descending neuron 30 defining the polarization path 35 from spinal anode 20, with this cathode being placed adjacent to the body part to be stimulated, e.g., at the medial nerve adjacent the wrist for stimulation of the peripheral nerve segment associated with control of the target body part.

The goal is to polarize the portion 30" of the descending neuron 30 along the polarization path 35 between the spinal anode 20 and the peripheral cathode 26, the key part of the polarization circuit 33. In operation, the spinal current flow establishes the tsDCS stimulation of the spinal cord and the descending nerve current flow establishes the polarization path 35 for treating spasticity of the target body part.

As indicated in FIGS. 3A and 4A, we have found that in order to accommodate the revised resistive pathway, the desired 65/35% split now is achieved with resistor R having a value of 1250 Ohms (FIG. 3A: R=1250Ω; FIG. 4A: R5=1250Ω).

In this configuration, there is an anodal spinal electrode and a split cathode (placed spinally and peripherally), all connecting with and controlled by a single spinal source current I1. For treating spasticity, this controlled source provides constant current flow between the spinal anode and the spinal cathode and also between the spinal anode and the single peripheral cathode. This is a simpler circuit design than the four electrode type of FIGS. 3 and 4, but with less accuracy in accommodation of the moment-to-moment changes in the treatment system. In this embodiment, the split ratio is established between the polarization current 33 portion of the full spinal source current I1 (spinal anode 20 to peripheral cathode 26) and the spinal current portion (spinal anode to spinal cathode).

Returning to FIG. 3, it will be understood that if both sink electrodes (spinal and peripheral cathodes) are connected together, the currents that flow depend solely on the impedances of electrode connections and the time-varying impedances of the body. This is an uncontrolled method that may not be optimum. And the operator does not know what the actual impedances of the electrode contact to skin will be or is, or how it will change, in time or person to person. There are many variables to consider including moisture, skin properties, fatty tissue present, quality of contact, variability in electrode surface area contact, manufacturing process variation, and many others. It is therefore beneficial to provide the active control of the present invention to gain full control over system currents.

Figure 5:
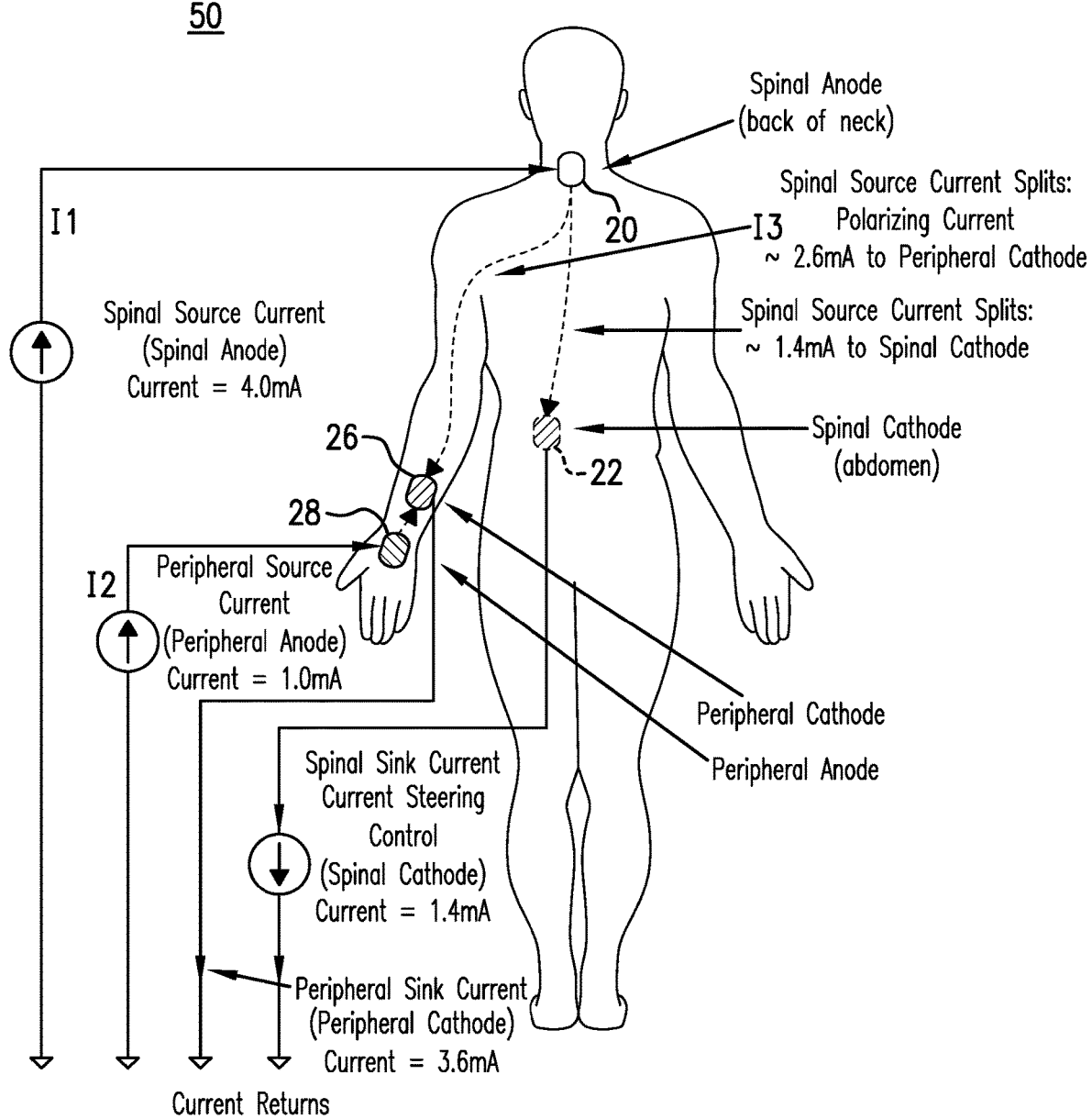
FIG. 5 illustrates anodal trans-spinal DC stimulation in an embodiment of the invention wherein current steering is implemented by spinal sink current in series with the spinal cathode and the ratio of spinal source current split is controlled and maintained via the spinal sink current.
Figure 6:
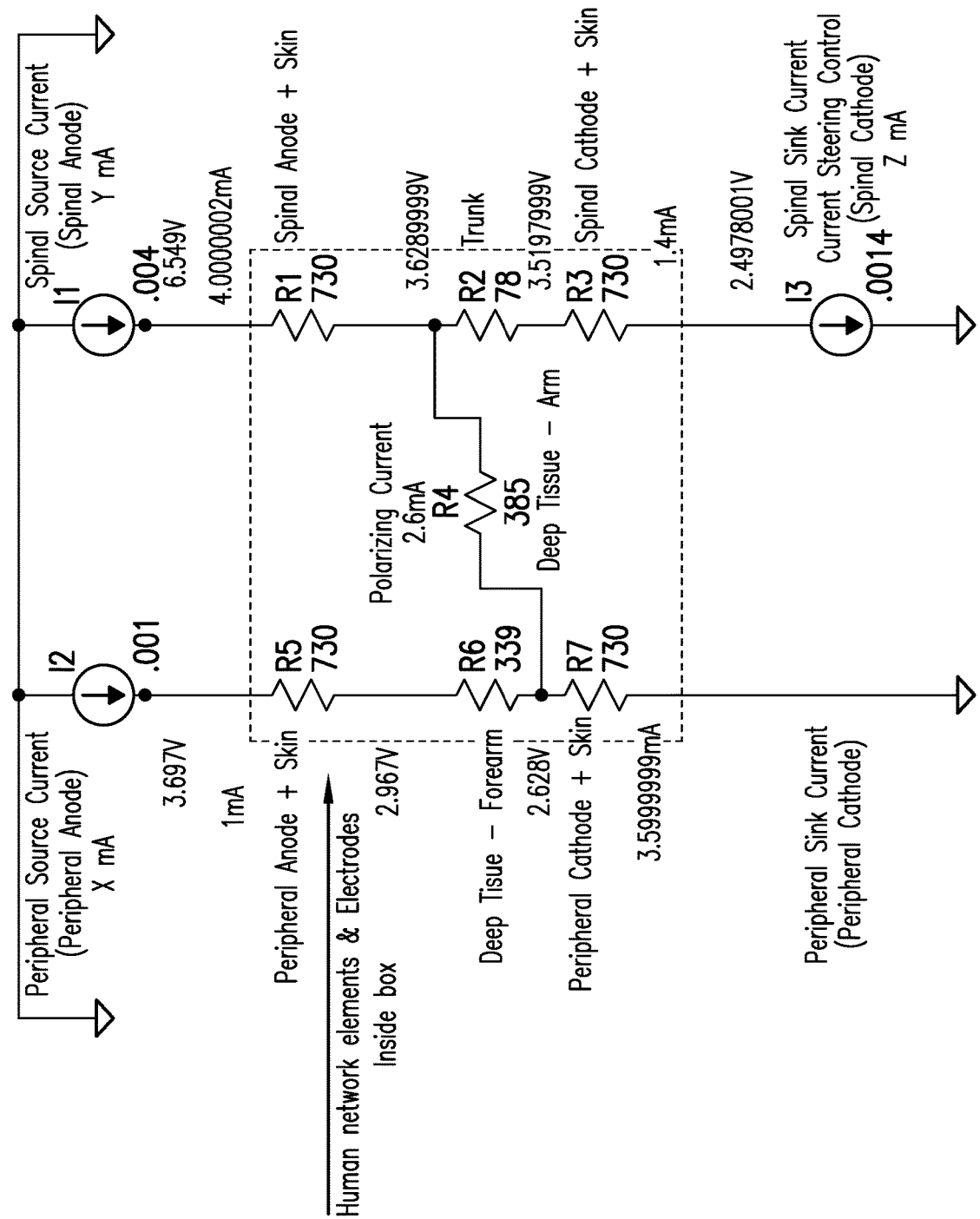
FIG. 6 illustrates anodal trans-spinal DC stimulation in an embodiment of the invention wherein current steering is implemented by spinal sink current in series with the spinal cathode and the ratio of spinal source current split is controlled and maintained by the applied spinal sink current.

Turning to FIGS. 5-6, in a further four electrode embodiment, we achieve precise control of the system currents through all four electrodes and skin interfaces, which allows for optimization of the therapeutic effect. As shown, the two anode electrodes spinal 20 and peripheral 28 source current into the body and two cathode electrodes spinal 22 and peripheral 26 sink current from the body.

In this illustrative embodiment we describe the control algorithms and circuits to steer these currents as desired in time. We apply low level direct current through the body using the two pairs of electrodes (four electrodes) to achieve desired therapeutic effects. This embodiment provides high accuracy steering of electrical current in a neurostimulation device. In the disclosed embodiment, three current sources offer precise control of the currents through each of the four electrodes. This precise control of current through all four electrode contacts, accommodating varying impedances throughout the stimulation circuit, allows for greater control over therapeutic interventions. For example, the ratio of the polarizing current to the spinal current will remain constant throughout a treatment despite changes of skin and tissue impedances over time.

It will now be appreciated that the device of FIGS. 5 and 6 enables improved steering of electrical current in a neurostimulation treatment, and works by passing a low level direct current through the body using the two pairs of electrodes (four electrodes) to achieve the desired therapeutic effects, achieving precise control of the currents through each electrode, where two electrodes source current into the body and two sink current. The precise control of current through all four contacts allows for the optimization of the therapeutic effect. This embodiment provides more precise steering of electrical current in a neurostimulation treatment of the invention.

At the same time, it is only possible to actively control three current sources into four electrode locations (nodes). The fourth node's current is then a summation of the currents into the net and a subtraction of the current out of the net. For example, if one sources 1 mA and 4 mA and one desires to sink 1.4 mA, the remaining fourth electrode must sink 3.6 mA. In this arrangement, the fourth electrode is left uncontrolled, even if all of the system impedances are not known.

Figure 5A:
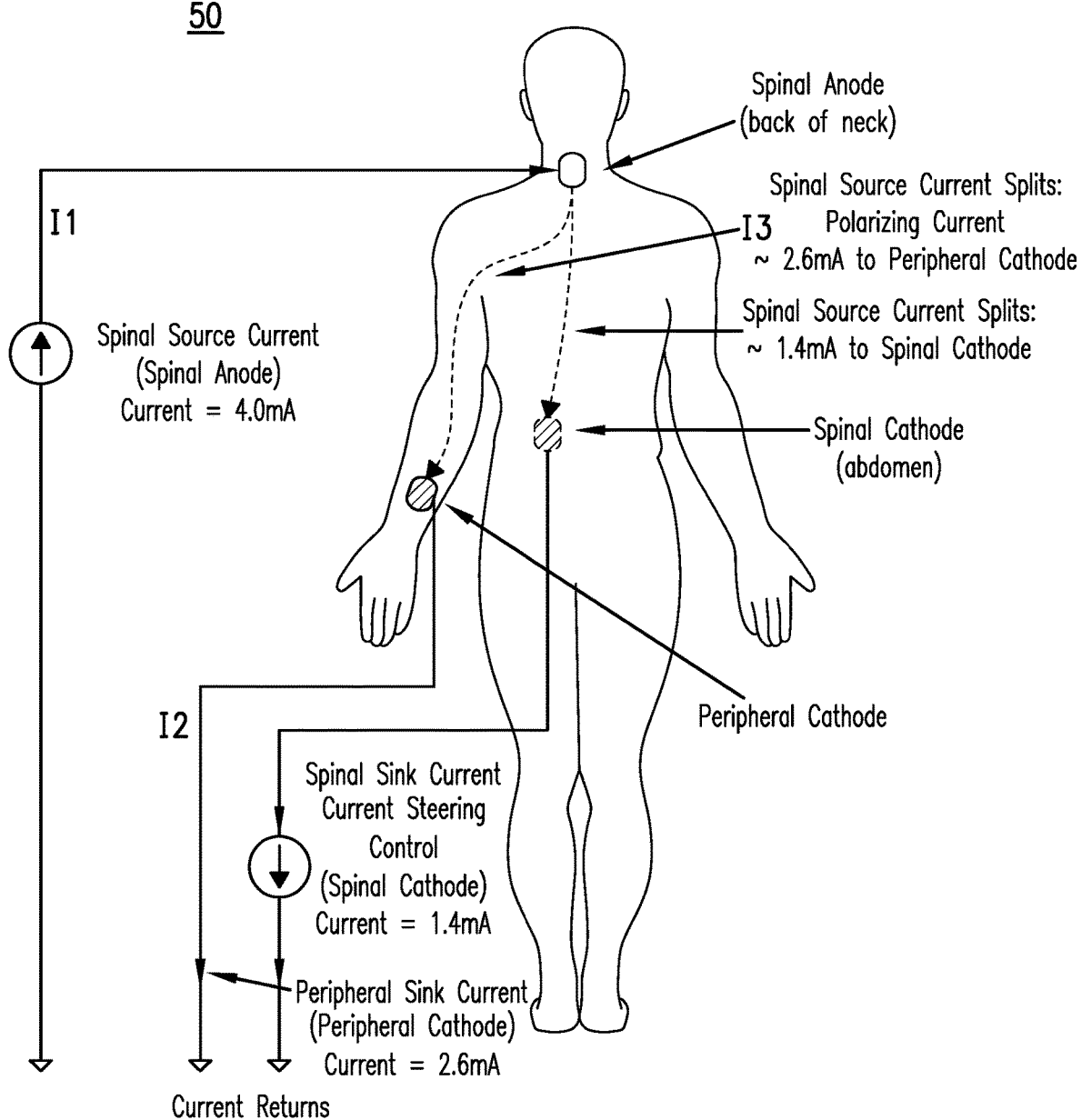
FIG. 5A illustrates anodal trans-spinal DC stimulation in an embodiment of the invention with spinal source and sink constant sources. Current steering is implemented by spinal sink current in series with the spinal cathode and the ratio of spinal source current split is controlled and maintained by the spinal sink current.
Figure 6A:
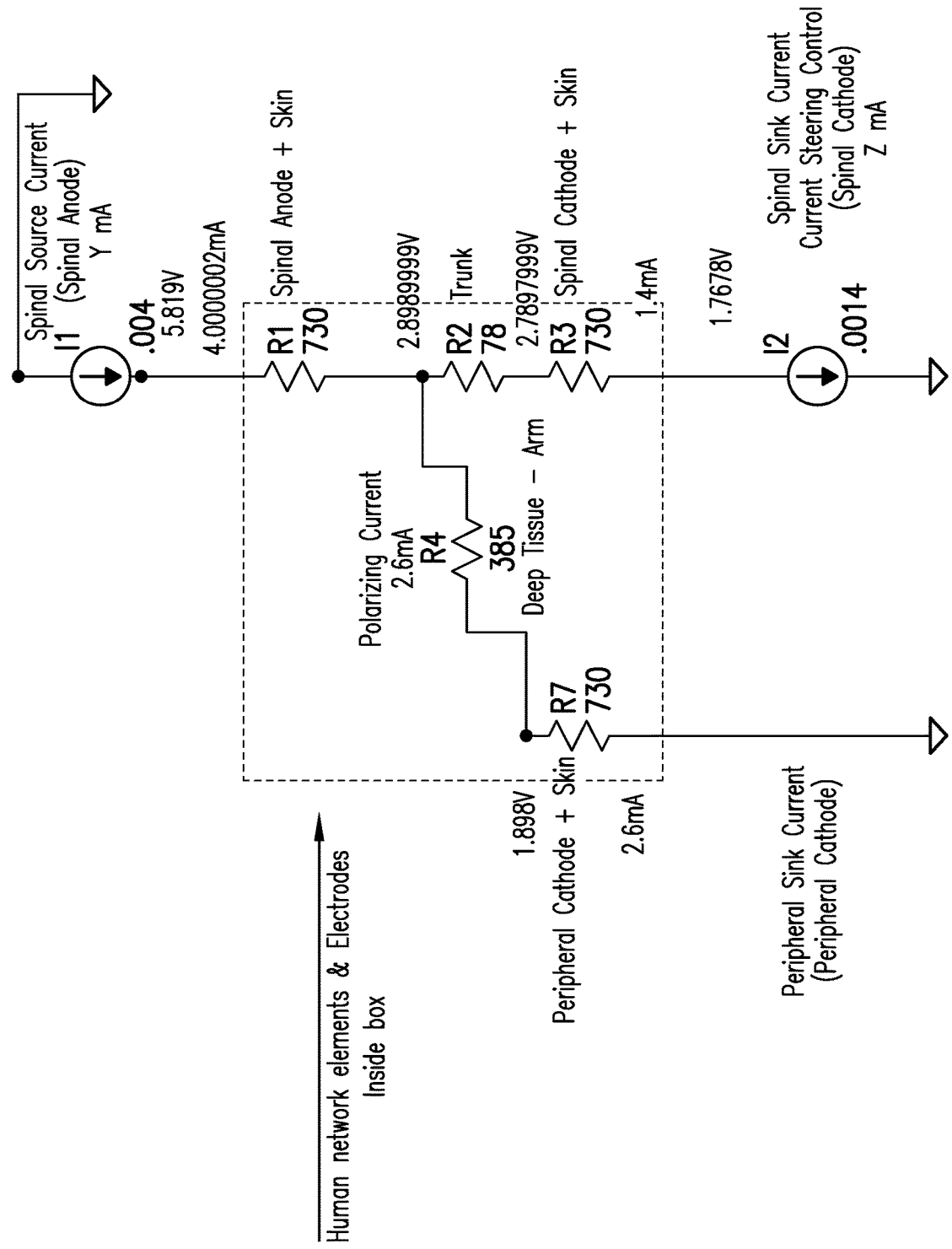
FIG. 6A illustrates anodal trans-spinal DC stimulation in an embodiment of the with spinal source and sink, and current steering is implemented by spinal sink current in series with the spinal cathode. The ratio of spinal source current split is controlled and maintained via the spinal sink current.

In the illustration of FIGS. 5 and 6, there are three constant current sources, one for the spinal source current, one for the peripheral source current and one for the spinal sink current. In the case of a simpler device implementation, shown in FIGS. 5A and 6A, the peripheral constant current source and the peripheral anode are eliminated, dispensing with the local direct stimulation of the peripheral nerve segment of the target muscle. Now two constant current sources address circuit changes of the entire circuit, albeit without he same specificity.

In FIGS. 5 and 6, we illustrate control algorithms in the case where we source X mA peripheral source current through the peripheral anode 28 and Y mA spinal source current through the spinal anode and we sink Z mA spinal current through the spinal cathode. In this algorithm, we can control Z mA through the sink electrode and, therefore, the sink current through the peripheral cathode is X+Y−Z.

Figure 7:
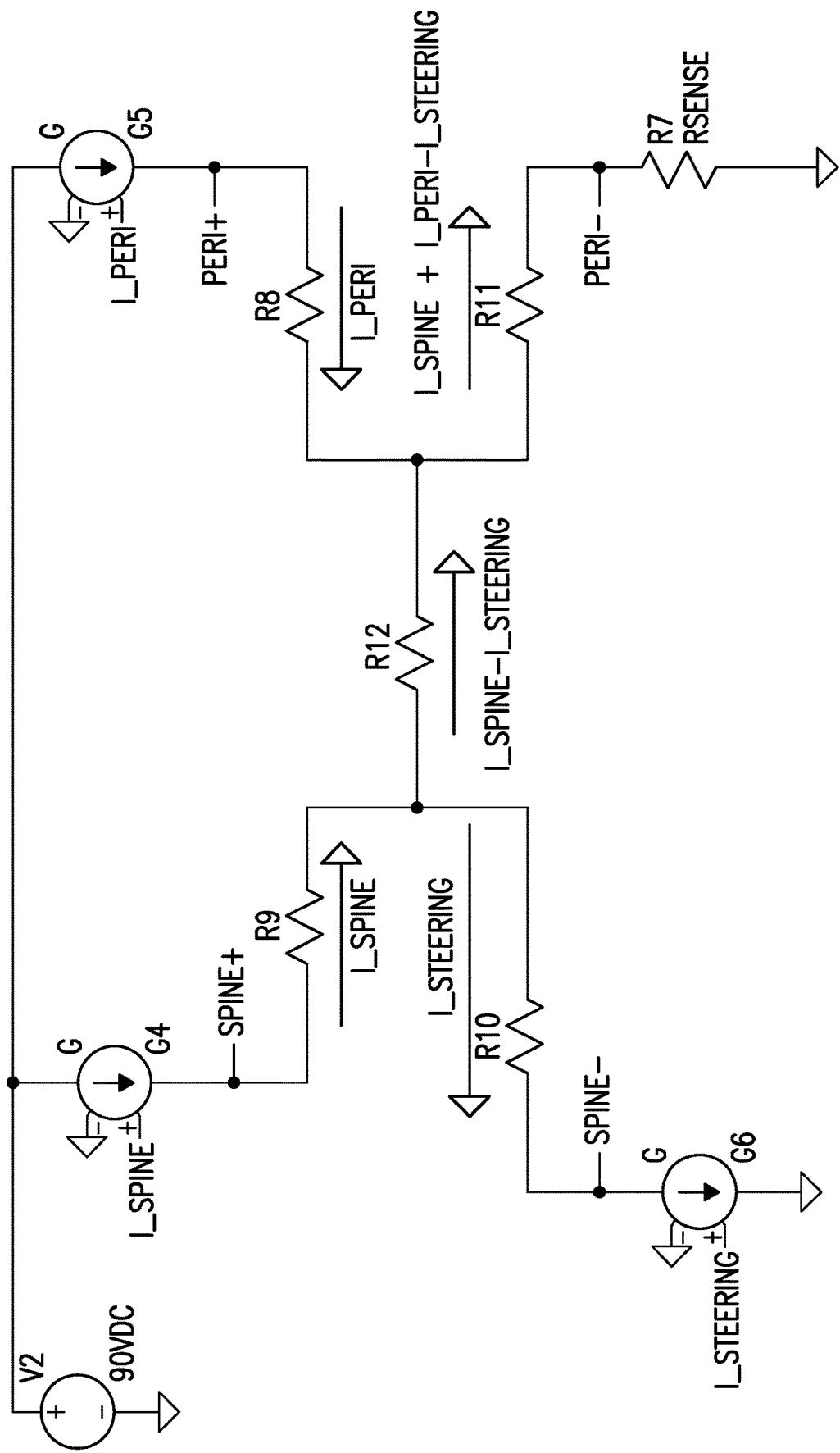
FIG. 7 illustrates a configuration for current steering of the invention, in which three currents G4, G5, G6 are directly controlled, while the current in R7 is indirectly controlled as a function of the three controlled currents G4, G5. This configuration works when voltage at "SPINET" is higher than voltage at "PERI-".

FIG. 7 is a more detailed illustrative circuit embodiment of FIG. 6. The three current sources represented by G4, G5, and G6 are transconductance amplifiers. The control signals to G4, G5 and G6 are I_SPINE, I_PERI and I_STEERING respectively. These signals are voltages from a digital to analog converter (DAC) which, in turn, receives a control digital value from a microprocessor 51 of controller 52. The microprocessor implements algorithms for calculating the desired Spinal Source Current, Peripheral Source Current and Spinal Sink Current (for current steering) described above. R8-R12 represent the human network as shown in FIG. 6. The current sources G4 and G5 need to be high voltage compliance to overcome the initial high impedances of the electrode-skin interface. The high voltage is supplied by V2.

Figure 8:
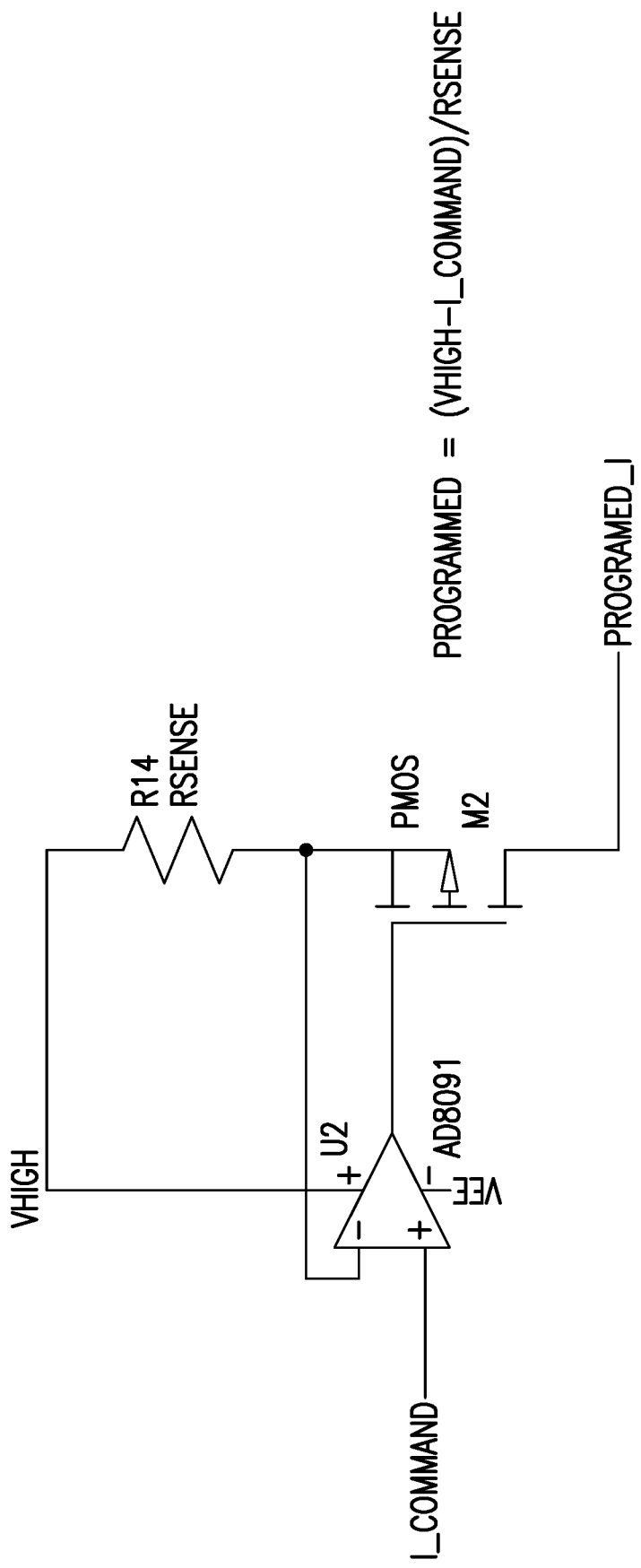
FIG. 8 illustrates a 'High Side' current control circuit of the invention.

FIG. 8 is a circuit embodiment of 'High Side' transconductance amplifiers G4 and G5 of FIG. 7. I_COMMAND is a generic voltage input represented by I_SPINE and I_PERI of FIG. 7. PROGRAMMED_I is the resulting current. This current control circuit is 'High Side' because it has high voltage compliance.

Figure 9:
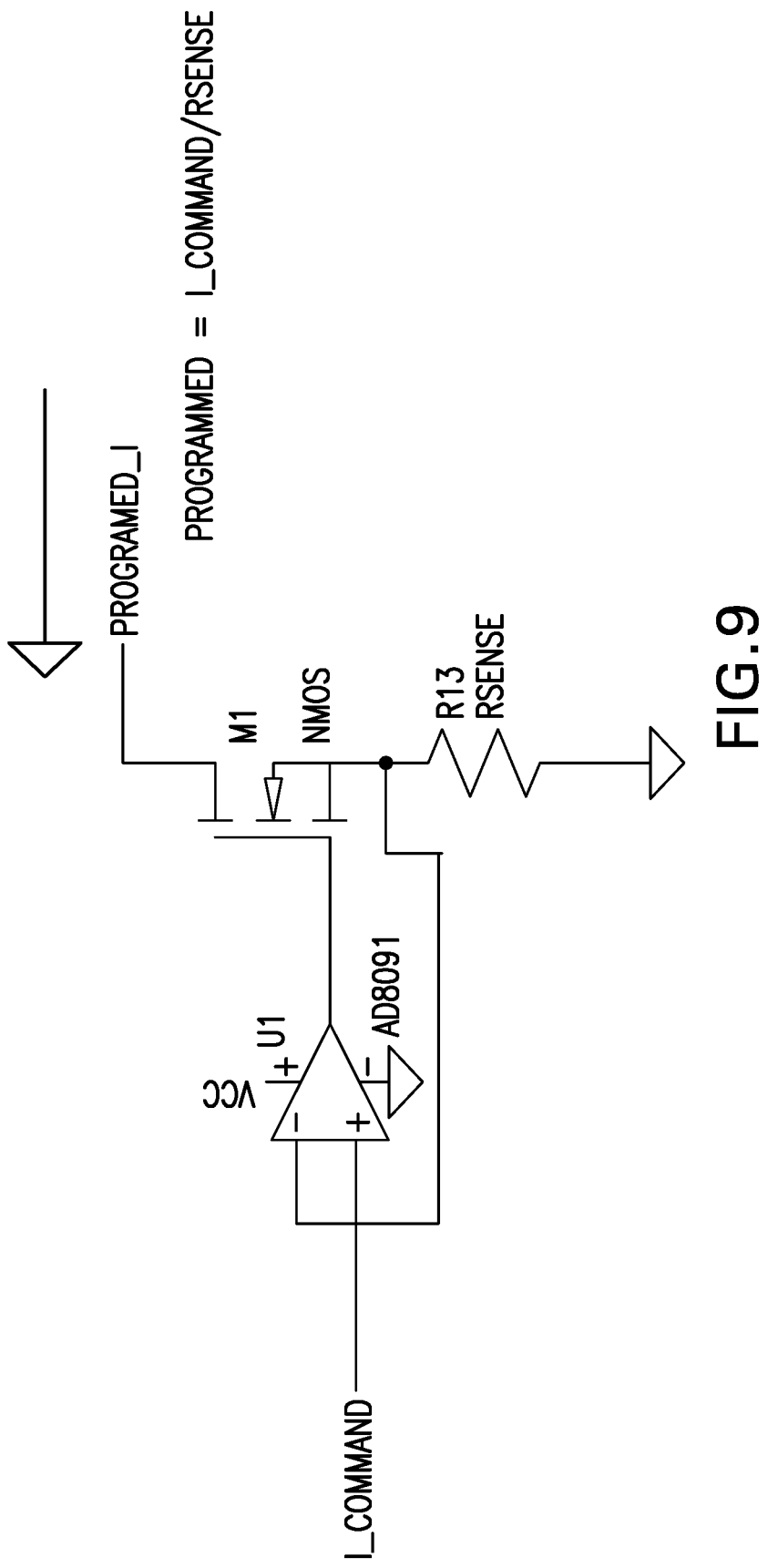
FIG. 9 illustrates a 'Side' current control circuit of the invention.

FIG. 9 is a circuit embodiment of 'low Side' transconductance amplifier G6 of FIG. 7. I_COMMAND is a generic voltage input represented by I_STEERING of FIG. 7. PRO- GRAMMED_I is the resulting current. This current control circuit is 'low Side' because it controls currents returning to common through a cathode.

Another aspect of the invention we make Z a function of Y so that Z=a*Y where a is typically between 0.2 and 0.8. Once again we know we need to control one sink with a*Y or the other with ((1−a)*Y)+X.

Another aspect of the invention covers where we make Z a function of X and Y so that Z=a*(X+Y) where a is typically between 0.2 and 0.8. Once again we know if we need to control one sink with a*(X+Y) or the other with (1−a)*(X+Y).

Another aspect of this invention covers where X and Y are functions of time, X(t) and Y(t) and Z is also a function of time. 'a' may also be a function of time. Time functions may be pulsed constant current DC monophasic, pulsed constant current charge balanced biphasic, pulsed constant current charge imbalanced biphasic and pulsed constant current balanced biphasic with interphase delay.

Another aspect of this invention covers a plurality of spinal and peripheral electrodes, both anode and cathode, each electrode in series with its own constant current source for further refinement of current focality across the spinal cord and peripheral nerve. The activation of the electrodes may vary with time producing a dynamic focality pattern. In another aspect, an array of small electrodes each with its own constant current source enable finely defining current paths across the spine.

Another aspect of this invention covers where X and Y and Z may be influenced by other conditions such as a feedback device to sense force, temperature, or vital signs from the human body. Another aspect of this invention covers where X and Y and Z are controlled by a function that monitors voltage to minimize discomfort or any noted hazardous condition.

In practice of the present invention, the following is an illustrative method for treatment of a spastic hand in a seated patient. The method features anodal spinal electrode and cathodal proximal electrode at median nerve to decrease muscle tone of a rigid hand and fingers. This is shown by way of illustration and not as limitation of the spirit and scope of the present teachings.

Spinal electrode placement: the anode electrode placed over the cervical region to cover C6 to the upper edge of T1, as will be understood by a person skilled in the art. (Before placing each electrode, the skin should be thoroughly cleansed with mild soap and water.)

Abdominal electrode placement: cathode electrode placed over anterior abdominal skin or other location that is not a major neural location.

For illustration, for reduction of muscle tone, median nerve electrode placement of two separate electrodes: the distal electrode (toward the hand) as anode; the proximal electrode (toward the cervical enlargement) as cathode. These electrodes are placed over and define nerve segment 30', associated with control of the body part of interest, e.g., spastic hand, which for example includes placement over the front aspect of the wrist joint across and over a section of the median nerve 30.

Electromyography electrode placement: bipolar electrodes record EMG from thumb muscles, placed over the abductor pollicis brevis (APB).

Tuning the stimulator of FIGS. 1-2: The stimulator output is brought to threshold and reduced to produce no EMG activity from the nerve/muscle. In illustrative practice of these teachings, such as about 4 mA at the spinal-abdominal circuit and about 2-3.5 mA at the median nerve circuit achieves desired results in a human. However, in small subjects the branch values may converge, such as 2-2.5 mA at both the nerve and spinal column. In the case of such a subject, typically a child, the adjustable power source S would be adjusted to bring the spinal circuit to about 2-2.5 mA and the variable resistor VR1-VR2 would be adjusted, thus bringing the nerve electrode set also to about 2 mA. In this case the current ratio I1:I2 would be as low.

Typical treatment duration: The duration is for 20 min. (At beginning/end of treatment ramping up/down is applied for comfort.)

End of treatment: Turn the stimulator off (after ramping down to zero input). Inspect the skin under the electrodes for any skin changes.

Current at the spinal cord is first adjusted typically ranging 2-4 mA on average, depending on age and body type/size, and access to nerve, etc., as would be appreciated by a person skilled in the art. Generally, larger and stronger patients require higher current level, and the spinal cord accepts a higher dose versus the current at the more sensitive target nerve.

Such is the possible utility of the prior art described above. Meanwhile the present invention is directed to improvements in application of the tsDCS/pDCS concept for real world systems for reliable commercial use by trained technicians in a medical office. Novel improvements are set forth below over the prior art.

In embodiments of the present invention, we provide control algorithms and circuits to steer currents as desired over time. For patient comfort the currents are often increased from zero to some precise and controllable level, typically less than 5 mA. During this ramp time, these currents are safe and the process minimizes discomfort or feeling of electrical shock. It is also possible to provide a varying DC signal during ramp up as will accelerate accommodation of the current passing through the skin barrier. Continuous constant current or even a pulsed constant current stimulation may be applied to drive embodiments of the invention.

While these teachings have been described in terms of specific embodiments, it will be evident in view of the foregoing description that numerous alternatives, modifications and variations will be apparent to those skilled in the art. Accordingly, these teachings are intended to encompass all such alternatives, modifications and variations which fall within the scope and spirit of the present teachings, and according to such claims as they are allowed after successful prosecution of this and non-provisional applications based hereon in whole or in part.

The invention claimed is:

1. A direct current (DC) neurostimulation system for providing trans-spinal direct current stimulation at a spinal location associated with modulating control of a target body part of a sentient being, and for providing direct current stimulation of a peripheral nerve associated with control of the target body part, configured to deliver stimulation via electrodes at skin interfaces, to treat a neurological condition of the being, comprising:

a spinal stimulation component configured to provide a spinal circuit associated with modulating control of a target body part of a being, for defining an active spinal pole at one polarity at a skin-surface spinal location for a first spinal electrode and a distal spinal pole at an opposite polarity at a distal skin-surface location for a second spinal electrode, for providing a spinal current flow, with said active and distal spinal poles communicating via a spinal neural pathway of said being;

a peripheral stimulation component configured to provide a proximal peripheral pole at said opposite polarity at a skin surface peripheral location for a peripheral electrode adjacent to a peripheral nerve associated with control of the target body part, said active spinal pole and said proximal peripheral pole communicating via a connecting neural pathway;

said spinal and peripheral stimulation components further configured to define a polarization circuit for providing polarization current flow on said connecting neural pathway for stimulating the peripheral nerve located between said active spinal pole at said one polarity and said proximal peripheral pole at said opposite polarity; and a controller component having a power source and configured for setting the polarity of said poles for one of up-regulation and down-regulation of the neurological condition of said being, and further configured to provide and actively control said polarization current flow in said polarization circuit by direct comparison with said spinal current flow in said spinal circuit, for real-time regulation of said polarization current flow in said polarization circuit and said spinal current flow in said spinal circuit and in said spinal and connecting neural pathways, for real-time controlled regulation of said target body part to treat said neurological condition, wherein said controller component is further configured to split and maintain said controlled current flows with said polarization current flow at a greater value than said spinal current flow, with said split between said polarization and said spinal circuits approximately 65/35%+/−20%.

2. A direct current (DC) neurostimulation system for providing trans-spinal direct current stimulation at a spinal location associated with modulating control of a target body part of a sentient being, and for providing direct current stimulation of a peripheral nerve associated with control of the target body part, configured to deliver stimulation via electrodes at skin interfaces, to treat a neurological condition of the being, comprising:

a spinal stimulation component configured to provide a spinal circuit associated with modulating control of a target body part of a being, for defining an active spinal pole at one polarity at a skin-surface spinal location for a first spinal electrode and a distal spinal pole at an opposite polarity at a distal skin-surface location for a second spinal electrode, for providing a spinal current flow, with said active and distal spinal poles communicating via a spinal neural pathway of said being;

a peripheral stimulation component configured to provide a proximal peripheral pole at said opposite polarity at a skin surface peripheral location for a peripheral electrode adjacent to a peripheral nerve associated with control of the target body part, said active spinal pole and said proximal peripheral pole communicating via a connecting neural pathway;

said spinal and peripheral stimulation components further configured to define a polarization circuit for providing polarization current flow on said connecting neural pathway for stimulating the peripheral nerve located between said active spinal pole at said one polarity and said proximal peripheral pole at said opposite polarity; and a controller component having a power source and configured for setting the polarity of said poles for one of up-regulation and down-regulation of the neurological condition of said being, and further configured to provide and actively control said polarization current flow in said polarization circuit by direct comparison with said spinal current flow in said spinal circuit, for real-time regulation of said polarization current flow in said polarization circuit and said spinal current flow in said spinal circuit and in said spinal and connecting neural pathways, for real-time controlled regulation of said target body part to treat said neurological condition, wherein said power source provides at least one constant current source, said controller component providing resistive current steering, having resistor R, in series with the distal spinal pole, wherein the ratio of spinal source current split is controlled by resistor R.

3. The system of claim 1 wherein said peripheral component further comprises a pair of peripheral stimulation poles further including a distal peripheral pole not at said opposite polarity at a skin surface peripheral location for a distal peripheral electrode and defining an anode and cathode pair of peripheral poles, for forming a peripheral stimulation circuit for stimulating an area associated with said peripheral nerve not stimulated by said polarization circuit, wherein said proximal peripheral pole is one of said peripheral pair of poles, said controller component configured for accommodating at least four skin-surface electrodes.

4. A direct current (DC) neurostimulation system for providing trans-spinal direct current stimulation at a spinal location associated with modulating control of a target body part of a sentient being, and for providing direct current stimulation of a peripheral nerve associated with control of the target body part, configured to deliver stimulation via electrodes at skin interfaces, to treat a neurological condition of the being, comprising:

a spinal stimulation component configured to provide a spinal circuit associated with modulating control of a target body part of a being, for defining an active spinal pole at one polarity at a skin-surface spinal location for a first spinal electrode and a distal spinal pole at an opposite polarity at a distal skin-surface location for a second spinal electrode, for providing a spinal current flow, with said active and distal spinal poles communicating via a spinal neural pathway of said being;

a peripheral stimulation component configured to provide a proximal peripheral pole at said opposite polarity at a skin surface peripheral location for a peripheral electrode adjacent to a peripheral nerve associated with control of the target body part, said active spinal pole and said proximal peripheral pole communicating via a connecting neural pathway;

said spinal and peripheral stimulation components further configured to define a polarization circuit for providing polarization current flow on said connecting neural pathway for stimulating the peripheral nerve located between said active spinal pole at said one polarity and said proximal peripheral pole at said opposite polarity; and a controller component having a power source and configured for setting the polarity of said poles for one of up-regulation and down-regulation of the neurological condition of said being, and further configured to provide and actively control said polarization current flow in said polarization circuit by direct comparison with said spinal current flow in said spinal circuit, for real-time regulation of said polarization current flow in said polarization circuit and said spinal current flow in said spinal circuit and in said spinal and connecting neural pathways, for real-time controlled regulation of said target body part to treat said neurological condition, and further comprising a power source supplying controlled flows of direct current in said spinal and polarization circuits, and providing dynamic current control at said spinal anode and at said spinal cathode, in a three electrode embodiment, and at least at said spinal anode and at said spinal cathode, in an embodiment with more than three electrodes.

5. The system of claim 4 further comprising in a multi-site neurostimulation system configured for pairing trans-spinal direct current stimulation of the spinal cord (tsDCS) with direct current stimulation of the peripheral nerve (pDCS) leading to the target body part, wherein the controller is further configured to pass low level direct current through the body to achieve therapeutic effects for patients having neurologic conditions.

6. The system of claim 3 having three circuits, spinal, peripheral and polarization, and further configured to provide resistive control in one leg of one of these circuits with current split between polarization and spinal circuits 65/35%, ranging about +/−10%.

7. The system of claim 6 further including resistive current control in the low voltage spinal (return) side of the spinal circuit.

8. The system of claim 3 wherein the controller component is configured to provide constant current control independent of the time-varying loads at the electrode skin interfaces and in the patient's neural pathways connecting between system electrodes.

9. The system of claim 3 wherein said active spinal pole is an anode, wherein said controller component is further configured to provide dynamic current control at: at least one of the spinal anode, in a three skin-surface system, and at least one at the active spinal pole as a spinal anode and at a peripheral anode of the peripheral circuit, in a four skin-surface system.

10. The system of claim 3 further comprising constant current nodes at the peripheral current source and at the spinal current source and at the spinal cathode, wherein the peripheral cathode action follows as it is determined by the control of the peripheral and spinal anodes and spinal cathode.

11. The system of claim 3 wherein the controller component is further configured to measure current through both the spinal and peripheral anodes in real time, and the polarizing current and the spinal cathode current are one of the set of metered and calculated.

12. The system of claim 3 further configured to provide three constant current sources variously to the spinal, polarizing and peripheral circuits, wherein constant current source sinks are placed as follows: one source in series on the "high" side of the spinal circuit, one source in series on the "high" side of the peripheral circuit, and one sink in series on the "low" side of the spinal circuit, in a four electrode configuration.

13. The system of claim 3 said controller component further configured to provide three constant current sources variously to the spinal, polarizing and peripheral circuits, wherein constant current source sinks are placed as follows: one source in series on the "high" side of the spinal circuit, one source in series on the "high" side of the peripheral circuit, and one sink in series on the "low" side of the spinal circuit, in a four electrode configuration, wherein the "low" side current sink in the spinal circuit is replaced with a resistor to steer a greater portion of the spinal current to the polarizing circuit.

14. The system of claim 1 utilizing one of the set of varying, pulsed and constant current DC.

15. A method for operating a DC neurostimulation system for providing trans-spinal direct current stimulation at a spinal location associated with control of a target body part, and direct current stimulation of the peripheral nerve associated with control of the target body part, with a power source supplying controlled flows of direct current in spinal and resulting polarization circuits, comprising the step of splitting current between the polarization and spinal circuits approximately 65/35%+/−10%.

16. The method of claim 15 wherein said controller component provides controlled flows of direct current in said spinal and polarization circuits and providing dynamic current control at said spinal anode and at said spinal cathode in a three electrode embodiment and at said spinal anode, at said spinal cathode and at said peripheral anode in a four electrode embodiment.

17. The method of claim 15 wherein said system is configured for utilizing one of the set of pulsed constant current DC monopolar and constant current DC biphasic, and providing a plurality of spinal and peripheral electrodes, both anode and cathode, each electrode in series with its own constant current source for further refinement of current focality across the spinal cord and peripheral nerve, further including one of wherein the activation of the electrodes may vary with time producing a dynamic focality pattern and wherein array of small electrodes each with its own constant current source enable finely defining current paths across the spine.

18. The method of claim 15 further including the step of implementation of control algorithms from the set including:
  a: in the case where we source X mA peripheral source current through the peripheral anode 28 and Y mA spinal source current through the spinal anode and we sink Z mA spinal current through the spinal cathode, to can control Z mA through the sink electrode and, therefore, the sink current through the peripheral cathode is X+Y−Z; and
  b: wherein three current sources represented by G4, G5, and G6 are transconductance amplifiers, and the control signals to G4, G5 and G6 are I_SPINE, I_PERI and I_STEERING respectively, which signals are voltages from a system digital to analog converter (DAC) which, in turn, receives a control digital value from the system microprocessor, wherein the microprocessor implements algorithms for calculating the desired Spinal Source Current, Peripheral Source Current and Spinal Sink Current (for current steering), wherein the current sources G4 and G5 need to be high voltage compliance to overcome the initial high impedances of the electrode-skin interface, with high voltage supplied by V2; and
  c: wherein with the 'High Side' transconductance amplifiers G4 and G5, I_COMMAND is a generic voltage input represented by I_SPINE and I_PERI; and PROGRAMMED_I is the resulting current, having high voltage compliance; and
  d: wherein in a circuit embodiment of 'Low Side' transconductance amplifier G6, I_COMMAND is a generic voltage input represented by I_STEERING, and PROGRAMMED_I is the resulting current, for controlling currents returning to common through a cathode; and
  e: wherein Z is a function of Y so that Z=a*Y where a is typically between 0.2 and 0.8, and where there is a need to control one sink with a * Y or the other with ((1−a)*Y)+X; and f: wherein Z is a function of X and Y so that Z=a*(X+Y) is typically between 0.2 and 0.8, and where there is a need to control one sink with a* (X+Y) or the other with (1−a) * (X+Y); and g: where X and Y are functions of time, X(t) and Y(t) and Z is also a function of time, and 'a' may also be a function of time and the time functions may be pulsed constant current DC monophasic, pulsed constant current charge balanced biphasic, pulsed constant current charge imbalanced biphasic and pulsed constant current balanced biphasic with interphase delay; and h: further including the step wherein where X and Y and Z may be influenced by other conditions such as a feedback device to sense force, temperature, or vital signs from the human body, and wherein X and Y and Z are controlled by a function that monitors voltage to minimize discomfort or any noted hazardous condition.

19. The method of claim 15 wherein said controller component is further configured having one of constant current control and resistive current control, and providing the step of real-time current control to said controlled current flows, and further providing the step of steering a greater portion of said spinal current flow to said polarizing circuit in real time.

20. The system of claim 2 wherein said controller component is further configured having one of constant current control and resistive current control and providing real-time current control to said controlled current flows, and further configured to steer a greater portion of said spinal current flow to said polarizing circuit in real time.

* * * * *